（12）United States Patent
Pestlin et al.

(10) Patent No.: US 7,579,158 B2
(45) Date of Patent: Aug. 25, 2009

(54) CELLULAR RETINOIC ACID BINDING PROTEIN II AS A MARKER FOR BREAST CANCER

(75) Inventors: Gabriele Pestlin, München (DE); Herbert Andres, Penzberg (DE); Peter Berndt, Basel (CH); Marie-Luise Hagmann, Penzberg (DE); Johann Karl, Peissenberg (DE); Hanno Langen, Steinen (DE); Werner Zolg, Weilheim-Unterhausen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/294,176

(22) Filed: Dec. 5, 2005

(65) Prior Publication Data

US 2006/0141543 A1 Jun. 29, 2006

Related U.S. Application Data

(63) Continuation of application No. PCT/EP2004/006029, filed on Jun. 4, 2004.

(30) Foreign Application Priority Data

Jun. 6, 2003 (EP) .................................. 03012942

(51) Int. Cl.
G01N 33/53 (2006.01)
G01N 33/68 (2006.01)
G01N 33/96 (2006.01)
G01N 33/574 (2006.01)

(52) U.S. Cl. ...................................... 435/7.1; 435/7.23
(58) Field of Classification Search .................... 435/7.1
See application file for complete search history.

(56) References Cited

U.S. PATENT DOCUMENTS 5,871,909 A 2/1999 Astrom et al.
2003/0124128 A1 * 7/2003 Lillie et al. .............. 424/155.1

FOREIGN PATENT DOCUMENTS

| WO | WO 00/60076 | | 10/2000 |
| WO | WO 02/23200 A2 | | 3/2002 |
| WO | WO 02/059377 A2 | | 8/2002 |
| WO | WO 02/077176 A2 | | 10/2002 |
| WO | WO 02/101075 A2 | | 12/2002 |
| WO | WO 03004989 | * | 1/2003 |
| WO | WO 03004989 A2 | * | 1/2003 |

OTHER PUBLICATIONS

Clinton et al (Biomed Sci Instrum. 2003; 39:408-14).*
Answers.com, "Blood", p. 1-19.*
Tockman et al (Cancer Res., 1992, 52:2711s-2718s).*
Gaub et al (J of Histochemistry & Cytochemistry, 1998, 46:1103-1111).*
Zeweig et al, Clinical Chemistry, 1993, 39:561-577.*
Who, "Screening for Breast Cancer," May 10, 2002.
Bruck, C. et al., "Purification of Mouse Monoclonal Antibodies from Ascitic Fluid by DEAE Affi-Gel Blue Chromatography," Methods I Enzymology, vol. 12 (1986) 587-596.
Budhu, A. et al., "Direct Channeling of Retinoic Acid between Cellular Retinoic.Acid Receptor Sensitizes Mammary Carcinoma Cells to Retinoic Acid-Induced Growth Arrest," Molecular and Cellular Biology, vol. 22, No. 8 Apr. 2002, p. 2632-2641.
Carney, P. et al., "Individual and Combined Effects of Age, Breast Density, and Hormone Replacement Therapy Use on the Accuracy of Screening Mammography," Ann Intern Med. 2003; 138: 168-175.
Chen, G. et al., "Discordant Protein and mRNA Expression in Lung Adenocarcinomas," Molecular & Cellular Proteomics 1 (2002) 304-313.
Diamandis, E. et al., eds., Immunoassay, 1996, Academic Press, Boston.
Duffy, M.J. et al., "Clinical Uses of Tumor Markers: A Critical Review," Critical Reviews in Clinical Laboratory Sciences, 38(3):225-262(2001).
Esserman, L. et al., "Improving the Accuracy of Mammography: Volume and Outcome Relationships," Journal of the National Cancer Institute, vol. 94, No. 5, Mar. 6, 2002.
Galfre, G. et al., "Preparation of Monoclonal Antibodies: Strategies and Procedures," Methods in Enzymology, vol. 73 (1981) 3-46.
Jing, Y. et al., "The Cellular Retinoic Acid Binding Protein II Is a Positive Regulator of Retinoic Acid Signaling in Breast Cancer Cells," Cancer Research 57, 1668-1672, May 1, 1997.
Kleywegt, G. et al., "Crystal structures of cellular retinoic acid binding proteins I and II in complex with all-trans-retionic acid and a synthetic retinoid," Structure 1994, vol. 2, No. 12, p. 1241-1258.
Kuerer, H. et al., "Identification of Distinct Protein Expression Patterns in Bilateral Matched Pair Breast Ductal Fluid Specimens from Women with Unilaterial Invasive Breast Carcinoma," Cancer 95(2002) 2276-2282.
Siegenthaler, G. et al., "Expression of CRABP-1 and -II in Human Epidermal Cells," Biochem, J. (1992) 287, 383-389.
Singletary, S. et al., "Revision of the American Joint Committee on Cancer Staging System for Breast Cancer," Journal of Clinical Oncology, Vo. 20, No. 17 (Sep. 1, 2002)L pp. 3628-3636.
Sobin, L. H. et al., Wittekind, Ch. (eds): TNM Classification of Malignant Tumours, fifth edition, 1997.

(Continued)

Primary Examiner—Laura B Goddard
(74) Attorney, Agent, or Firm—Marilyn L. Amick; Roche Diagnostics Operations, Inc.

(57) ABSTRACT

The present invention relates to the diagnosis of breast cancer. It discloses the use of protein cellular retinoic acid binding protein II in the diagnosis of breast cancer. It relates to a method for diagnosis of breast cancer from a liquid sample, derived from an individual by measuring cellular retinoic acid binding protein II in said sample. Measurement of cellular retinoic acid binding protein II can, e.g., be used in the early detection or diagnosis of breast cancer.

6 Claims, 3 Drawing Sheets

OTHER PUBLICATIONS

Studier, F. et al., "Use of T7 RNA Polymerase to Direct Expression of Cloned Genes," Methods in Enzymology, vol. 185 (1990) 60-89.

Tijssen, P. (1985) Practice and Theory of Enzyme Immunoassays, Elsevier, Amsterdam.

Untch, M. et al., "Tumor Markers in Breast Cancer," J. Lab. Med. 25 (2001) 343-352.

Vahlquist, A. et al., "Increased Concentrations of 3, 4-Didehydroretinol and Retinoic Acid-Binding Protein (CRABPII) in Human Squamous Cell Carcinoma and Keratoacanthoma But Not in Basal Cell Carcinoma of the Skin," Journal of Investigative Dermatology 106 (1996) 1070-1074.

Vo. H. et al., "Transcriptional Regulation of Retinoic Acid Responsive Genes by Cellular Retinoic Acid Binding Protein-II Modulates RA Mediated Tumor Cell Proliferation and Invasion," Anticancer Research 18:217-224 (1998).

Wang, Y. et al., "Immunohistochemical Identification of Retinoic Acid Receptor ά(RARά) and Cellular Retinoic Acid Binding Protein II (CRABPII) in Human Breast Carcinoma," Laboratory Investigation 78 (1889) 30 A.

Widschwendter, M. et al., "Interaction of Retinoic Acid and Interferon-ά in Breast Cancer Cell Lines," Anticancer Research 16: 369-374 (1996).

Wulfkuhle, J. et al., "Proteomics of Human Breast Ductal Carcinoma in Situ," Cancer Research 62, 6740-6749, Nov. 15, 2002.

Zweig, M. et al., "Receiver-Operating Characteristic (ROC) Plots: A Fundamental Evaluation Tool in Clinical Medicine," Clin. Chem. 39/4, 561-577 (1993).

National Cancer Institute, Cancer Facts, Fact Sheet 5.18 (1998) 1-5.

Anderson, L., Seilhamer, J., "A comparison of selected mRNA and protein abundances in human liver", Electrophoresis 1997, 18, 533-537.

Greenbaum, D., Colangelo, C., Williams, K., Gerstein, M., "Comparing protein abundance and mRNA expression levels on a genomic scale", Genome Biology 2003, vol. 4, Issue 9, Article 117.1-117.8.

Gygi, S., Rochon, Y., Franza, B., Aebersold, R., "Correlation between Protein and mRNA Abundance in Yeast", Molecular and Cellular Biology, Mar. 1999, pp. 1720-1730.

* cited by examiner

SEQUENCE LISTING

<160> NUMBER OF SEQ ID NOS: 1

<210> SEQ ID NO 1
<211> LENGTH: 137
<212> TYPE: PRT
<213> ORGANISM: Homo sapiens

<400> SEQUENCE: 1

```
Pro Asn Phe Ser Gly Asn Trp Lys Ile Ile Arg Ser Glu Asn Phe Glu
1               5                   10                  15

Glu Leu Leu Lys Val Leu Gly Val Asn Val Met Leu Arg Lys Ile Ala
                20                  25                  30

Val Ala Ala Ser Lys Pro Ala Val Glu Ile Lys Gln Glu Gly Asp
            35                  40                  45

Thr Phe Tyr Ile Lys Thr Ser Thr Thr Val Arg Thr Thr Glu Ile Asn
        50                  55                  60

Phe Lys Val Gly Glu Glu Phe Glu Glu Gln Thr Val Asp Gly Arg Pro
65                  70                  75                  80

Cys Lys Ser Leu Val Lys Trp Glu Ser Glu Asn Lys Met Val Cys Glu
```

-continued

```
                85                  90                  95
Gln Lys Leu Leu Lys Gly Glu Gly Pro Lys Thr Ser Trp Thr Arg Glu
            100                 105                 110

Leu Thr Asn Asp Gly Glu Leu Ile Leu Thr Met Thr Ala Asp Asp Val
            115                 120                 125

Val Cys Thr Arg Val Tyr Val Arg Glu
            130                 135
```

CELLULAR RETINOIC ACID BINDING PROTEIN II AS A MARKER FOR BREAST CANCER

RELATED APPLICATIONS

This application is a continuation of PCT/EP2004/006029 filed Jun. 4, 2004 and claims priority to European application EP 03012942.3 filed Jun. 6, 2003.

FIELD OF THE INVENTION

The present invention relates to the diagnosis of breast cancer. It discloses the use of cellular retinoic acid binding protein II in the diagnosis of breast cancer. Furthermore, it especially relates to a method for diagnosis of breast cancer from a liquid sample, derived from an individual by measuring cellular retinoic acid binding protein II in said sample. Measurement of cellular retinoic acid binding protein II can, e.g., be used in the early detection or diagnosis of breast cancer.

BACKGROUND OF THE INVENTION

Cancer remains a major public health challenge despite progress in detection and therapy. Amongst the various types of cancer, breast cancer (BC) is one of the most frequent cancers among women in the Western world.

The earlier cancer can be detected/diagnosed, the better is the overall survival rate. This is especially true for BC. The prognosis in advanced stages of tumor is poor. More than one third of the patients will die from progressive disease within five years after diagnosis, corresponding to a survival rate of about 40% for five years. Current treatment is only curing a fraction of the patients and clearly has the best effect on those patients diagnosed in an early stage of disease.

With regard to BC as a public health problem, it is essential that more effective screening and preventative measures for breast cancer will be developed.

The earliest detection procedures available at present for breast cancer involve using clinical breast examination and mammography. However, significant tumor size must typically exist before a tumor is palpable or can be detected by a mammogram. The density of the breast tissue and the age are important predictors of the accuracy of screening mammography. The sensitivity ranges from 63% in women with extremely dense breasts to 87% in women with almost entirely fatty breasts. The sensitivity increases with age from 69% in women of about 40 years of age to 83% in women 80 years and older (Carney, P. A., et al., Ann. Intern. Med. 138 (3) (2003) 168-175). Only 20-25% of mammographically detected abnormalities that are biopsied prove to be malignant. The visualization of precancerous and cancerous lesions represents the best approach to early detection, but mammography is an expensive test that requires great care and expertise both to perform and in the interpretation of results (WHO, Screening for Breast Cancer, May 10, 2002; Esserman, L., et al., J. Natl. Cancer Inst. 94 (2002) 369-375).

In the recent years a tremendous amount of so-called breast specific or even so-called breast cancer specific genes has been reported. The vast majority of the corresponding research papers or patent applications are based on data obtained by analysis of RNA expression patterns in breast (cancer) tissue versus a different tissue or an adjacent normal tissue, respectively. Such approaches may be summarized as differential mRNA display techniques.

As an example for data available from mRNA-display techniques, WO 00/60076 shall be mentioned and discussed. This application describes and claims more than two hundred isolated polynucleotides and the corresponding polypeptides as such, as well as their use in the detection of BC. However, it is general knowledge that differences on the level of mRNA are not mirrored by the level of the corresponding proteins. A protein encoded by a rare mRNA may be found in very high amounts and a protein encoded by an abundant mRNA may nonetheless be hard to detect and find at all (Chen, G., et al., Molecular and Cellular Proteomics, 1.4 (2002) 304-313). This lack of correlation between mRNA-level and protein level is due to reasons like mRNA stability, efficiency of translation, stability of the protein, etc.

There also are recent approaches investigating the differences in protein patterns between different tissues or between healthy and diseased tissue in order to identify candidate marker molecules which might be used in the diagnosis of BC. Wulfkuhle et al. Cancer Research 62 (2002) 6740-6749 have identified fifty-seven proteins which were differentially expressed between BC tissue and adjacent normal tissue. No data from liquid samples obtained from an individual are reported.

WO 02/23200 reports about twelve breast cancer-associated spots as found by surface-enhanced laser desorption and ionization (SELDI). These spots are seen more frequently in sera obtained from patients with BC as compared to sera obtained from healthy controls. However, the identity of the molecule(s) comprised in such spot, e.g their sequence, is not known.

Nipple aspirate fluid (NAF) has been used for many years as a potential non-invasive method to identify breast cancer-specific markers. Kuerer et al. compared bilateral matched pair nipple aspirate fluids from women with unilateral invasive breast carcinoma by 2D gel electrophoresis (Kuerer, H. M., et al., Cancer 95 (2002) 2276-2282). 30 to 202 different protein spots were detected in the NAF of breasts suffering from breast carcinoma and not in the matched NAF of the healthy breasts. These spots were detected by a gel image analysis. But the identity of the protein spots is not known.

Despite the large and ever growing list of candidate protein markers in the field of BC, to date clinical/diagnostic utility of these molecules is not known. In order to be of clinical utility a new diagnostic marker as a single marker should be at least as good as the best single marker known in the art. Or, a new marker should lead to a progress in diagnostic sensitivity and/or specificity either if used alone or in combination with one or more other markers, respectively. The diagnostic sensitivity and/or specificity of a test is best assessed by its receiver-operating characteristics, which will be described in detail below.

At present, only diagnostic blood tests based on the detection of cancer antigen 15-3 (CA 15-3), a tumor-associated mucin, and carcinoembryonic antigen (CEA), a tumor associated glycoprotein, are available to assist diagnosis in the field of BC. CA 15-3 is usually increased in patients with advanced breast cancer. CA 15-3 levels are rarely elevated in women with early stage breast cancer (Duffy, M. J., Critical Reviews in Clinical Laboratory Sciences 38 (2001) 225-262). Cancers of the ovary, lung and prostate may also raise CA 15-3 levels. Elevated levels of CA 15-3 may be associated with non-cancerous conditions, such as benign breast or ovary disease, endometriosis, pelvic inflammatory disease, and hepatitis. Pregnancy and lactation can also cause CA 15-3 levels to raise (National Cancer Institute, Cancer Facts, Fact Sheet 5.18 (1998) 1-5). The primary use of CEA is in monitoring colon cancer, especially when the disease has metastasized. However, a variety of cancers can produce elevated levels of CEA, including breast cancer.

Due to the lack of organ and tumor specificity, neither measurement of CA 15-3 nor measurement of CEA are recommended for screening of BC. These tumor markers are helpful diagnostic tools in follow-up care of BC patients (Untch, M., et al., J. Lab. Med. 25 (2001) 343-352).

Whole blood, serum, plasma, or nipple aspirate fluid are the most widely used sources of sample in clinical routine. The identification of an early BC tumor marker that would allow reliable cancer detection or provide early prognostic information could lead to a diagnostic assay that would greatly aid in the diagnosis and in the management of this disease. Therefore, an urgent clinical need exists to improve the diagnosis of BC from blood. It is especially important to improve the early diagnosis of BC, since for patients diagnosed early on chances of survival are much higher as compared to those diagnosed at a progressed stage of disease.

It was the task of the present invention to investigate whether a new marker can be identified which may aid in BC diagnosis.

SUMMARY OF THE INVENTION

Surprisingly, it has been found that use of the marker cellular retinoic acid binding protein II can at least partially overcome the problems known from the state of the art.

The present invention therefore relates to a method for the diagnosis of breast cancer comprising the steps of a) providing a liquid sample obtained from an individual, b) contacting said sample with a specific binding agent for cellular retinoic acid binding protein II under conditions appropriate for formation of a complex between said binding agent and cellular retinoic acid binding protein II, and c) correlating the amount of complex formed in (b) to the diagnosis of breast cancer Another preferred embodiment of the invention is a method for the diagnosis of breast cancer comprising the steps of a) contacting a liquid sample obtained from an individual with a specific binding agent for cellular retinoic acid binding protein II under conditions appropriate for formation of a complex between said binding agent and cellular retinoic acid binding protein II, and b) correlating the amount of complex formed in (a) to the diagnosis of breast cancer.

As the skilled artisan will appreciate, any such diagnosis is made in vitro. The patient sample is discarded afterwards. The patient sample is merely used for the in vitro diagnostic method of the invention and the material of the patient sample is not transferred back into the patient's body. Typically, the sample is a liquid sample.

DESCRIPTION OF THE INVENTION

The cellular retinoic acid binding protein II (CRABP-II) (Swiss-PROT: P29373) is characterized by the sequence given in SEQ ID NO:1. This sequence translates to a molecular weight of 15,562 Da and to an isoelectric point at pH 5.43.

The two isoforms of cellular retinoic acid binding proteins (CRABP-I and -II) were first characterized by Siegenthaler et al. 1992. CRABP-II was shown to be the major isoform, highly expressed in human epidermis by fibroblasts and keratinocytes (Siegenthaler, G., Biochemical Journal 287 (1992) 383-389).

An increased concentration of CRABP-II was found in keratoacanthoma and squamous cell cancer but not in basal cell carcinoma of the skin by Anders et al. (Anders, V., et al., Journal of Investigative Dermatology 106 (1996) 1070-1074).

In the cytoplasm, CRABP-II regulates the intracellular retinoic acid (RA) concentration, transport, and metabolism. It has been demonstrated that RA induced CRABP-II mRNA levels 2 fold in squamous cell cancer by transcriptional upregulation (Vo, H. P., Crowe, D. L., Anticancer Research 18 (1998) 217-224).

The presence of CRABP-II in human breast cancer cells was first described by Wang et al. 1998. They localized CRABP-II in human breast cancer cells by immunohistochemistry (Wang, Y., et al., Laboratory Investigation 78 (1998) 30 A).

The function of CRABP-II in mammary carcinoma cells was described by Budhu and Noy 2002 (Molecular and Cellular Biology 22 (2002) 2632-2641). The cytosolic CRABP-II undergoes a nuclear localization upon binding RA and interacts with retinoic acid receptor (RAR) by building a short lived CRABP-II-RAR-complex. The overexpression of CRABP-II in MCF7 mammary cell lines enhances their sensitivity to retinoic acid-induced growth inhibition (Budhu, A. S., Noy, N., supra).

In a first proteomics analysis of matched normal ductal/ lobular units and ductal carcinoma in situ (DCIS) of the human breast Wulfkuhle et al. (Cancer Research 62 (2002) 6740-6749) identified fifty-seven proteins that were differentially expressed in normal and precancerous cells. The level of CRABP-II was reported to be five times higher in DCIS than in normal cells. A comparable increase has been reported for as many as 23 proteins. But no further investigations were carried out, e.g. whether CRABP-II could be detected in liquid samples (Wulfkuhle, J. D. et al., supra).

CRABP-II has been mentioned in different patent applications besides a large number of genes and their proteins for diagnosing or prognosing the development or progression of breast cancer (WO 02/77176, WO 02/101075, WO 02/59377). But the diagnostic application has not been described.

As obvious to the skilled artisan, the present invention shall not be construed to be limited to the full-length protein CRABP-II of SEQ ID NO:1. Physiological or artificial fragments of CRABP-II, secondary modifications of CRABP-II, as well as allelic variants of CRABP-II are also encompassed by the present invention. Artificial fragments preferably encompass a peptide produced synthetically or by recombinant techniques, which at least comprises one epitope of diagnostic interest consisting of at least 6 contiguous amino acids as derived from the sequence disclosed in SEQ ID NO:1. Such fragment may advantageously be used for generation of antibodies or as a standard in an immunoassay. More preferred the artificial fragment comprises at least two epitopes of interest appropriate for setting up a sandwich immunoassay.

In preferred embodiments, the novel marker CRABP-II may be used for monitoring as well as for screening purposes.

When used in patient monitoring the diagnostic method according to the present invention may help to assess tumor load, efficacy of treatment and tumor recurrence in the follow-up of patients. Increased levels of CRABP-II are directly correlated to tumor burden. After chemotherapy a short term (few hours to 14 days) increase in CRABP-II may serve as an indicator of tumor cell death. In the follow-up of patients (from 3 months to 10 years) an increase of CRABP-II can be used as an indicator for tumor recurrence.

In a preferred embodiment the diagnostic method according to the present invention is used for screening purposes. I.e., it is used to assess subjects without a prior diagnosis of BC by measuring the level of CRABP-II and correlating the level measured to the presence or absence of BC.

The staging of cancer is the classification of the disease in terms of extent, progression, and severity. It groups cancer patients so that generalizations can be made about prognosis and the choice of therapy.

Today, the TNM system is the most widely used classification of the anatomical extent of cancer. It represents an internationally accepted, uniform staging system. There are three basic variables: T (the extent of the primary tumor), N (the status of regional lymph nodes) and M (the presence or absence of distant metastases). The TNM criteria are published by the UICC (International Union Against Cancer) (Sobin, L. H., Wittekind, Ch. (eds): TNM Classification of Malignant Tumours, fifth edition, 1997). The staging system for breast cancer has recently been revised (Singletary, S. E., et al., Journal of Clinical Oncology 20 (2002) 3628-3636).

What is especially important is, that early diagnosis of BC translates to a much better prognosis. Therefore, best prognosis have those patients as early as in stage $T_{is}$, N0, M0 or T1-3; N0; M0, if treated properly have a more than 90% chance of survival 5 years after diagnosis as compared to a 5-years survival rate of only 18% for patients diagnosed when distant metastases are already present.

In the sense of the present invention early diagnosis of BC refers to a diagnosis at a pre-cancerous state (DCIS) or at a tumor stage where no metastases at all (neither proximal nor distal), i.e., $T_{is}$, N0, M0 or T1-4; N0; M0 are present. $T_{is}$ denotes carcinoma in situ.

In a preferred embodiment CRABP-II is used to diagnose BC in a non metastatic stage, i.e., that diagnosis is made at stage $T_{is}$, N0, M0 or T1-3; N0; M0 (=$T_{is}$–3; N0; M0).

The diagnostic method according to the present invention is based on a liquid sample which is derived from an individual. Unlike to methods known from the art CRABP-II is specifically measured from this liquid sample by use of a specific binding agent.

A specific binding agent is, e.g., a receptor for CRABP-II, a lectin binding to CRABP-II or an antibody to CRABP-II. A specific binding agent has at least an affinity of $10^7$ l/mol for its corresponding target molecule. The specific binding agent preferably has an affinity of $10^8$ l/mol or even more preferred of $10^9$ l/mol for its target molecule. As the skilled artisan will appreciate the term specific is used to indicate that other biomolecules present in the sample do not significantly bind to with the binding agent specific for CRABP-II. Preferably, the level of binding to a biomolecule other than the target molecule results in a binding affinity which is only 10%, more preferably only 5% of the affinity of the target molecule or less. A most preferred specific binding agent will fulfill both the above minimum criteria for affinity as well as for specificity.

A specific binding agent preferably is an antibody reactive with CRABP-II. The term antibody refers to a polyclonal antibody, a monoclonal antibody, fragments of such antibodies, as well as to genetic constructs comprising the binding domain of an antibody. Any antibody fragment retaining the above criteria of a specific binding agent can also be used.

Antibodies are generated by state of the art procedures, e.g., as described in Tijssen (Tijssen, P., Practice and theory of enzyme immunoassays 11 (1990) the whole book, especially pages 43-78; Elsevier, Amsterdam). In addition, the skilled artisan is well aware of methods based on immunosorbents that can be used for the specific isolation of antibodies. By these means the quality of polyclonal antibodies and hence their performance in immunoassays can be enhanced. (Tijssen, P., supra, pages 108-115).

For the achievements as disclosed in the present invention monoclonal and polyclonal antibodies have been used. Polyclonal antibodies have been raised in rabbits. However, clearly also polyclonal antibodies from different species, e.g. rats or guinea pigs can also be used. Monoclonal antibodies have been produced using spleen cells from immunized mice. Since monoclonal antibodies can be produced in any amount required with constant properties, they represent ideal tools in development of an assay for clinical routine. The generation and use of monoclonal antibodies to CRABP-II in a method according to the present invention is yet another preferred embodiment.

As the skilled artisan will appreciate now, that CRABP-II has been identified as a marker which is useful in the diagnosis of BC, alternative ways may be used to reach a result comparable to the achievements of the present invention. For example, alternative strategies to generate antibodies may be used. Such strategies comprise amongst others the use of synthetic peptides, representing an epitope of CRABP-II for immunization. Preferably, a synthetic peptide comprises a subsequence of SEQ ID NO:1 which is specific for CRABP-II, i.e., which has a comparatively low homology to other/ related polypeptides. It is preferred that the synthetic peptide comprises a contiguous subsequence consisting of 5 to 25 amino acid residues of SEQ ID NO:1. More preferred, the peptide comprises a contiguous subsequence consisting of 10 to 15 amino acid residues of SEQ ID NO:1.

A very preferred subsequence of CRAP-II consists of the amino acid residues 85-96 of SEQ ID NO:1. A further preferred subsequence consists of the amino acid residues 106-120 of SEQ ID NO:1 and Cysteine residue added to its C-terminus for a facilitated coupling via SH-chemistry.

Alternatively, DNA immunization also known as DNA vaccination may be used.

For measurement the liquid sample obtained from an individual is incubated with the specific binding agent for CRABP-II under conditions appropriate for formation of a binding agent CRABP-II-complex. Such conditions need not be specified, since the skilled artisan without any inventive effort can easily identify such appropriate incubation conditions.

As a final step according to the method disclosed in the present invention the amount of complex is measured and correlated to the diagnosis of BC. As the skilled artisan will appreciate there are numerous methods to measure the amount of specific binding agent CRABP-II-complex all described in detail in relevant textbooks (cf., e.g., Tijssen P., supra, or Diamandis et al., eds. (1996) Immunoassay, Academic Press, Boston).

Preferably CRABP-II is detected in a sandwich type assay format. In such assay a first specific binding agent is used to capture CRABP-II on the one side and a second specific binding agent, which is labeled to be directly or indirectly detectable is used on the other side.

As mentioned above, it has surprisingly been found that CRABP-II can be measured from a liquid sample obtained from an individual sample. No tissue and no biopsy sample is required to apply the marker CRABP-II in the diagnosis of BC.

In a preferred embodiment the method according to the present invention is practiced with serum as liquid sample material.

In a further preferred embodiment the method according to the present invention is practiced with plasma as liquid sample material.

In a further preferred embodiment the method according to the present invention is practiced with whole blood as liquid sample material.

In a further preferred embodiment the method according to the present invention is practiced with nipple aspirate fluid as liquid sample material.

Whereas application of routine proteomics methods to tissue samples, leads to the identification of many potential marker candidates for the tissue selected, the inventors of the present invention have surprisingly been able to detect CRABP-II in a bodily fluid sample. Even more surprising they have been able to demonstrate that the presence of CRABP-II in such liquid sample obtained from an individual can be correlated to the diagnosis of breast cancer.

Antibodies to CRABP-II with great advantage can be used in established procedures, e.g., to detect breast cancer cells in situ, in biopsies, or in immunohistological procedures.

Preferably, an antibody to CRABP-II is used in a qualitative (CRABP-II present or absent) or quantitative (CRABP-II amount is determined) immunoassay.

Measuring the level of protein CRABP-II has proven very advantageous in the field of BC. Therefore, in a further preferred embodiment, the present invention relates to use of protein CRABP-II as a marker molecule in the diagnosis of breast cancer from a liquid sample obtained from an individual.

The term marker molecule is used to indicate that an increased level of the analyte CRABP-II as measured from a bodily fluid of an individual marks the presence of BC.

It is especially preferred to use the novel marker CRABP-II in the early diagnosis of breast cancer.

The use of protein CRABP-II itself, represents a significant progress to the challenging field of BC diagnosis. Combining measurements of CRABP-II with other known markers, e.g. CA 15-3 and CEA, or with other markers of BC presently known or yet to be discovered, leads to further improvements. Therefore in a further preferred embodiment the present invention relates to the use of CRABP-II as a marker molecule for breast cancer in combination with one or more marker molecules for breast cancer in the diagnosis of breast cancer from a liquid sample obtained from an individual. In this regard, the expression "one or more" denotes 1 to 10, preferably 1 to 5, more preferred 3. Preferred selected other BC markers with which the measurement of CRABP-II may be combined are CEA and CA 15-3. Most preferred, CRABP-II is used as part of a marker panel at least comprising CRABP-II and CA 15-3. Thus, a further preferred embodiment of the present invention is the use of the protein CRABP-II as a marker molecule for breast cancer in combination with one or more marker molecules for breast cancer in the diagnosis of breast cancer from a liquid sample obtained from an individual, whereby the at least one other marker molecule is CA 15-3.

Preferably, the inventive method is used with samples of patients suspected of suffering from breast cancer. An individual suspected of suffering from breast cancer is an individual for which other types of cancers have been excluded. Other cancers include but are not limited to cancers of the colon, lung, stomach, ovary, and prostate. A preferred embodiment of the invention is therefore a method for the diagnosis of breast cancer comprising the steps of a) providing a liquid sample obtained from an individual suspected of suffering from breast cancer, b) contacting said sample with a specific binding agent for cellular retinoic acid binding protein II under conditions appropriate for formation of a complex between said binding agent and cellular retinoic acid binding protein II, and c) correlating the amount of complex formed in (b) to the diagnosis of breast cancer.

Diagnostic reagents in the field of specific binding assays, like immunoassays, usually are best provided in the form of a kit, which comprises the specific binding agent and the auxiliary reagents required to perform the assay. The present invention therefore also relates to an immunological kit comprising at least one specific binding agent for CRABP-II and auxiliary reagents for measurement of CRABP-II.

Accuracy of a test is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease.

In each case, the ROC plot depicts the overlap between the two distributions by plotting the sensitivity versus 1-specificity for the complete range of decision thresholds. On the y-axis is sensitivity, or the true-positive fraction [defined as (number of true-positive test results) (number of true-positive+number of false-negative test results)]. This has also been referred to as positivity in the presence of a disease or condition. It is calculated solely from the affected subgroup. On the x-axis is the false-positive fraction, or 1-specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot. By convention, this area is always ≧0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Clinical utility of the novel marker CRABP-II has been assessed in comparison to and in combination with the established marker CA 15-3 using a receiver operator curve analysis (ROC; Zweig, M. H., and Campbell, G., Clin. Chem. 39 (1993) 561-577). This analysis has been based on well-defined patient cohorts consisting of 50 samples each from patients with invasive ductal or lobular carcinoma in T1-3; N0; M0, more progressed tumor, i.e., T4 and/or various severity of metastasis (N+ and/or M+), medullary, papillary, mucinous and tubular carcinoma, ductal carcinoma in situ, and healthy controls, respectively.

The diagnostic method based on measurement of CRABP-II alone in comparison to the established marker CA 15-3 alone has been found to have an at least as good a diagnostic accuracy (sensitivity/specificity profile) as demonstrated by the area under the curve.

The examples, sequence listing, and figures are provided to aid the understanding of the present invention, the true scope of which is set forth in the appended claims. It is understood that modifications can be made in the procedures set forth without departing from the spirit of the invention.

| Abbreviations | |
|---|---|
| ABTS | 2,2'-Azino-di-[3-ethylbenzthiazoline sulfonate (6)] diammonium salt |
| BSA | bovine serum albumin |
| cDNA | complementary DNA |
| CHAPS | (3-[(3-Cholamidopropyl)-dimethylammonio]-1-propane-sulfonate) |
| DMSO | dimethyl sulfoxide |
| DTT | dithiothreitol |
| EDTA | ethylene diamine tetraacetic acid |
| ELISA | enzyme-linked immunosorbent assay |
| HRP | horseradish peroxidase |
| IAA | iodacetamid |
| IgG | immunoglobulin G |
| IEF | isoelectric focussing |
| IPG | immobilized pH gradient |
| LDS | lithium dodecyl sulfate |
| MALDI-TOF | matrix-assisted laser desorption/ionisation-time of flight mass spectrometry |
| MES | mesityl,2,4,6-trimethylphenyl |
| OD | optical density |
| PAGE | polyacrylamide gel electrophoresis |
| PBS | phosphate buffered saline |
| PI | isoelectric point |
| RTS | rapid translation system |
| SDS | sodium dodecyl sulfate |
| UICC | International Union Against Cancer |

Specific Embodiments

EXAMPLE 1

Identification of Cellular Retinoic Acid Binding Protein II (CRABP-II) as a Potential Breast Cancer Marker Sources of Tissue In order to identify tumor-specific proteins as potential diagnostic markers for breast cancer, analysis of two different kinds of tissue is performed using proteomics methods.

In total, tissue specimen from 14 patients suffering from breast cancer are analyzed. From each patient two different tissue types are collected from therapeutic resections: Tumor tissue (>80% tumor) (T), and adjacent healthy tissue (N). The latter tissue type serves as matched healthy control sample. Tissues are immediately snap frozen after resection and stored at −80° C. before processing. Tumors are diagnosed by histopathological criteria.

Tissue Preparation 0.8-1.2 g of frozen tissue are put into a mortar and completely frozen by liquid nitrogen. The tissue is pulverized in the mortar, dissolved in the 10-fold volume (w/v) of lysis buffer (40 mM Na-citrate, 5 mM $MgCl_2$, 1% Genapol X-080, 0.02% Na-azide, Complete® EDTA-free [Roche Diagnostics GmbH, Mannheim, Germany, Cat. No. 1 873 580]) and subsequently homogenized in a Wheaton® glass homogenizer (20×loose fitting, 20×tight fitting). 3 ml of the homogenate are subjected to a sucrose-density centrifugation (10-60% sucrose) for 1 h at 4,500×g. After this centrifugation step three fractions are obtained. The fraction on top of the gradient contains the soluble proteins and is used for further analysis.

Immobilization of Monoclonal Antibody Anti-human Albumin on CNBr-activated Sepharose 4B Freeze-dried CNBr-activated Sepharose 4B (Amersham Biosciences, 17-0430-01) is reswollen and washed according to the instructions of the manufacturer. Monoclonal antibody directed against human albumin is dissolved in 0.1 M $NaHCO_3$, pH 8.3, 0.5 M NaCl, 10 mg/ml. One ml antibody solution is mixed with 1 ml reswollen CNBr-activated Sepharose 4B. The reaction time is 1 h. Blocking of the remaining active groups and washing of the gel is carried out according to the instructions of the manufacturer.

Depletion of Serum Albumin 7 ml anti-albumin gel is equilibrated in lysis buffer without Genapol X-080. 7 ml of the upper fraction of the sucrose-density centrifugation (see above, tissue preparation) are applied onto the column and washed through with lysis buffer without Genalpol X-080. The combined effluent is used for the isoelectric focussing experiments.

Isoelectric Focussing (IEF) and SDS-PAGE

For IEF, 3 ml of the HSA-depleted tissue preparation are mixed with 12 ml sample buffer (7 M urea, 2 M thiourea, 2% CHAPS, 0.4% IPG buffer pH 4-7, 0.5% DTT) and incubated for 1 h. The samples are concentrated in an Amicon® Ultra-15 device (Millipore GmbH, Schwalbach, Germany) and the protein concentration is determined using the Bio-Rad® protein assay (Cat. No. 500-0006; Bio-Rad Laboratories GmbH, München, Germany) following the instructions of the supplier's manual. To a volume corresponding to 1.5 mg of protein sample buffer is added to a final volume of 350 µl. This solution is used to rehydrate IPG strips pH 4-7 (Amersham Biosciences, Freiburg, Germany) overnight. The IEF is performed using the following gradient protocol: (1.) 1 minute to 500 V; (2.) 2 h to 3500 V; (3.) 22 h at constant 3500 V giving rise to 82 kVh. After IEF, strips are stored at −80° C. or directly used for SDS-PAGE.

Prior to SDS-PAGE the strips are incubated in equilibration buffer (6 M urea, 50 mM Tris/HCl, pH 8.8, 30% glycerol, 2% SDS), for reduction DTT (15 min, +50 mg DTT/10 ml), and for alkylation IAA (15 min, +235 mg iodacetamide/10 ml) is added. The strips are put on 12.5% polyacrylamide gels and subjected to electrophoresis at 1 W/gel and thereafter 1 h at 17 W/gel. Subsequently, the gels are fixed (50% methanol, 10% acetate) and stained overnight with Novex™ Colloidal Blue Staining Kit (Invitrogen, Karlsruhe, Germany, Cat No. LC6025, 45-7101)

Detection of CRABP-II as a Potential Marker for Breast Cancer

Figure 1:
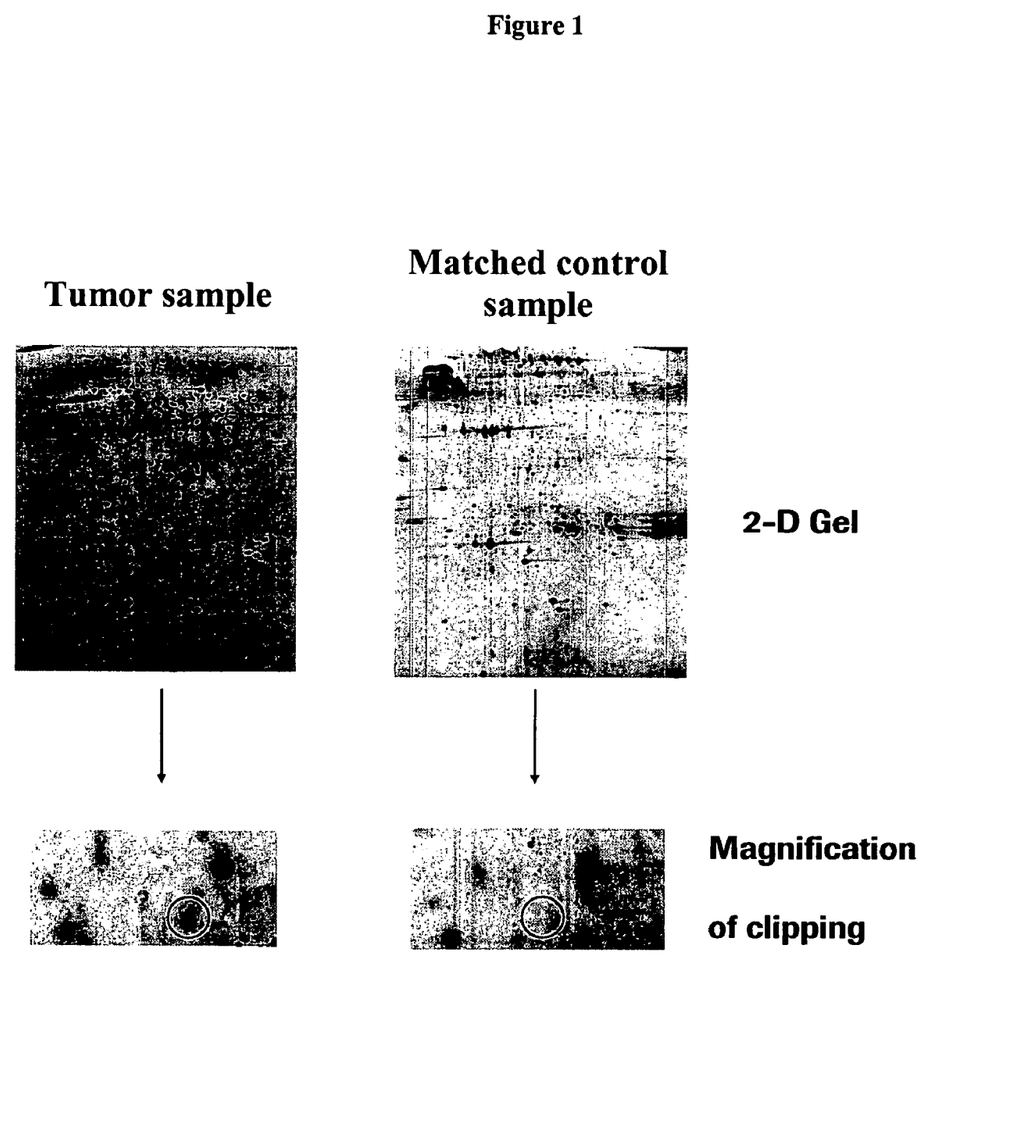
FIG. 1 shows a typical example of a 2D-gel, loaded with a tumor sample (left side), and a gel, loaded with a matched control sample (right side). The circle in the enlarged section of these gels indicates the position for the protein cellular retinoic acid binding protein II (CRABP-II). Using the same method this protein has not been detected in healthy tissue.

Each patient is analyzed separately by image analysis with the Proteome Weaver® software (Definiens AG, Germany, München). In addition, all spots of the gel are excised by a picking robot and the proteins present in the spots are identified by MALDI-TOF mass spectrometry (Ultraflex™ Tof/Tof, Bruker Daltonik GmbH, Bremen, Germany). For each patient, 4 gels from the tumor sample are compared with 4 gels each from adjacent tissue and analyzed for distinctive spots corresponding to differentially expressed proteins. By this means, protein CRABP-II is found to be specifically expressed or strongly overexpressed in tumor tissue and not detectable in healthy control tissue. It therefore—amongst many other proteins—qualifies as a candidate marker for use in the diagnosis of breast cancer.

EXAMPLE 2

Generation of Antibodies to the Breast Cancer Marker Protein CRABP-II

Polyclonal antibody to the breast cancer marker protein CRABP-II is generated for further use of the antibody in the measurement of serum and plasma and blood levels of CRABP-II by immunodetection assays, e.g. Western Blotting and ELISA Recombinant Protein Expression and Purification In order to generate antibodies to CRABP-II, recombinant expression of the protein is performed for obtaining immunogens. The expression is done applying a combination of the RTS 100 expression system and *E. coli*. In a first step, the DNA sequence is analyzed and recommendations for high yield cDNA silent mutational variants and respective PCR-primer sequences are obtained using the "ProteoExpert RTS *E. coli* HY" system. This is a commercial web-based service (www.proteoexpert.com). Using the recommended primer pairs, the "RTS 100 *E. coli* Linear Template Generation Set, His-tag" (Roche Diagnostics GmbH, Mannheim, Germany, Cat. No. 3186237) system to generate linear PCR templates from the cDNA for in-vitro transcription and expression of the nucleotide sequence coding for the CRABP-II protein is used. For Western-blot detection and later purification, the expressed protein contains a His-tag. The best expressing variant is identified. All steps from PCR to expression and detection are carried out according to the instructions of the manufacturer. The respective PCR product, containing all necessary T7 regulatory regions (promoter, ribosomal binding site and T7 terminator) is cloned into the pBAD TOPO® vector (Invitrogen, Karlsruhe, Germany, Cat. No. K 4300/01) following the manufacturer's instructions. For expression using the T7 regulatory sequences, the construct is transformed into *E. coli* BL 21 (DE 3) (Studier, F. W., et al., Methods Enzymol. 185 (1990) 60-89) and the transformed bacteria are cultivated in a 1 l batch for protein expression.

Purification of His-CRABP-II fusion protein is done following standard procedures on a Ni-chelate column. Briefly, 1 l of bacteria culture containing the expression vector for the His-CRABP-II fusion protein is pelleted by centrifugation. The cell pellet is resuspended in lysis buffer, containing phosphate,. pH 8.0, 7 M guanidium chloride, imidazole and thioglycerole, followed by homogenization using a Ultra-Turrax®. Insoluble material is pelleted by high speed centrifugation and the supernatant is applied to a Ni-chelate chromatographic column. The column is washed with several bed volumes of lysis buffer followed by washes with buffer, containing phosphate, pH 8.0 and urea. Finally, bound antigen is eluted using a phosphate buffer containing SDS under acid conditions.

In addition, CRABP-II protein is expressed and purified as described in Kleywegt, G. J. et al., Structure 2 (1994) 1241-1258, particularly page 1252 ("Protein preparation").

Peptide Synthesis

Peptides are synthesized and purified by means of state of the art chemistry.

The CRABP-II-peptide corresponding to positions 85-96 of SEQ ID NO:1 contains a cysteine residue. The peptide is further on also referred to as CRABP-II (85-96) or the CRABP-II (85-96) peptide.

To the CRABP-II-peptide corresponding to positions 106-120 of SEQ ID NO:1 a Cysteine residue is added at the C-terminus of the peptide. The peptide is further on also referred to as CRABP-II (106-120 Cys) or the CRABP-II (106-120 Cys) peptide.

Synthesis of Hemocyanin-peptide Conjugates for the Generation of Antibodies

Synthesis is carried out using heterobifunctional chemistry (maleimide/SH-chemistry).

The CRABP-II (85-96) peptide is coupled to 3-maleimidohexanoyl-N-hydroxysuccinimidester (MHS) activated hemocyanin. Similarly, the CRABP-II (106-120 Cys) peptide is coupled to 3-maleimidohexanoyl-N-hydroxysuccinimidester (MHS) activated hemocyanin. Hemocyanin is brought to 10 mg/ml in 100 mM NaH$_2$PO$_4$/NaOH, pH 7.2. Per ml hemocyanin 100 µl MHS (12.3 mg in DMSO) are added and incubated for 1 h. The sample is dialyzed over night against 100 mM NaH$_2$PO$_4$/NaOH, pH 6.5 and adjusted to 6 mg/ml with dialysis buffer. The CRABP-II (85-96) peptide or the CRABP-II (106-120 Cys) peptide is dissolved in DMSO (5 mg/ml for a peptide of 1,500 Da [Dalton]). Per ml MHS-activated hemocyanin (6 mg/ml) 20 µl of 100 mM EDTA, pH 7.0 and 100 µl of the cysteine-containing CRABP-II-peptide (85-96) or the CRABP-II (106-120 Cys) peptide are added. After 1 h the remaining maleimide groups are blocked by the addition of 10 µl 0.5 M cysteine/HCl per ml reaction mixture. This preparation is used for immunization without further purification.

Production of Monoclonal Antibodies Against the CRABP-II a) Immunization of Mice 12 week old A/J mice are initially immunized intraperitoneally with 100 µg CRABP-II or hemocyanin-peptide-conjugate (see above). This is followed after 6 weeks by two further intraperitoneal immunizations at monthly intervals. In this process each mouse is administered 100 µg CRABP-II or hemocyanin-peptide-conjugate adsorbed to aluminum hydroxide and $10^9$ germs of *Bordetella pertussis*. Subsequently the last two immunizations are carried out intravenously on the 3rd and 2nd day before fusion using 100 µg CRABP-II or hemocyanin-peptide-conjugate in PBS buffer for each.

b) Fusion and Cloning

Spleen cells of the mice immunized according to a) are fused with myeloma cells according to Galfre, G., and Milstein, C., Methods in Enzymology 73 (1981) 3-46. In this process ca. $1\times10^8$ spleen cells of the immunized mouse are mixed with $2\times10^7$ myeloma cells (P3X63-Ag8-653, ATCC CRL1580) and centrifuged (10 min at 300×g and 4° C.). The cells are then washed once with RPMI 1640 medium without foetal calf serum (FCS) and centrifuged again at 400×g in a 50 ml conical tube. The supernatant is discarded, the cell sediment is gently loosened by tapping, 1 ml PEG (molecular weight 4000, Merck, Darmstadt) is added and mixed by pipetting. After 1 min in a water-bath at 37° C., 5 ml RPMI 1640 without FCS is added drop-wise at room temperature within a period of 4-5 min. Afterwards 5 ml RPMI 1640 containing 10% FCS is added drop-wise within ca. 1 min, mixed thoroughly, filled to 50 ml with medium (RPMI 1640+10% FCS) and subsequently centrifuged for 10 min at 400×g and 4° C. The sedimented cells are taken up in RPMI 1640 medium containing 10% FCS and sown in hypoxanthine-azaserine selection medium (100 mmol/l hypoxanthine, 1 µg/ml azaserine in RPMI 1640+10% FCS). Interleukin 6 at 100 U/ml is added to the medium as a growth factor.

After ca. 10 days the primary cultures are tested for specific antibody. CRABP-II-positive primary cultures are cloned in 96-well cell culture plates by means of a fluorescence activated cell sorter. In this process again interleukin 6 at 100 U/ml is added to the medium as a growth additive.

c) Immunoglobulin Isolation from the Cell Culture Supernatants

The hybridoma cells obtained are sown at a density of $1\times10^5$ cells per ml in RPMI 1640 medium containing 10% FCS and proliferated for 7 days in a fermenter (Thermodux Co., Wertheim/Main, Model MCS-104XL, Order No. 144-050). On average concentrations of 100 µg monoclonal antibody per ml are obtained in the culture supernatant. Purification of this antibody from the culture supernatant is carried out by conventional methods in protein chemistry (e.g. according to Bruck, C., et al., Methods in Enzymology 121 (1986) 587-695).

Generation of Polyclonal Antibody:

a) Immunization

For immunization, a fresh emulsion of the protein solution (100 µg/ml CRABP-II or hemocyanin-peptide-conjugate comprising the CRABP-II (85-96) peptide or the CRABP-II (106-120 Cys) peptide) and complete Freund's adjuvant at the ratio of 1:1 is prepared. With respect to each peptide, each rabbit is immunized with 1 ml of the emulsion of the at days 1, 7, 14 and 30, 60 and 90. Blood is drawn and resulting anti-CRABP-II serum used for further experiments as described in Examples 3 and 4.

b) Purification of IgG (immunoglobulin G) from Rabbit Serum by Sequential Precipitation with Caprylic Acid and Ammonium Sulfate One volume of rabbit serum is diluted with 4 volumes of acetate buffer (60 mM, pH 4.0). The pH is adjusted to 4.5 with 2 M Tris-base. Caprylic acid (25 µl/ml of diluted sample) is added drop-wise under vigorous stirring. After 30 min the sample is centrifuged (13,000×g, 30 min, 4° C.), the pellet discarded and the supernatant collected. The pH of the supernatant is adjusted to 7.5 by the addition of 2 M Tris-base and filtered (0.2 µm).

The immunoglobulin in the supernatant is precipitated under vigorous stirring by the drop-wise addition of a 4 M ammonium sulfate solution to a final concentration of 2 M. The precipitated immunoglobulins are collected by centrifugation (8,000×g, 15 min, 4° C.).

The supernatant is discarded. The pellet is dissolved in 10 mM $NaH_2PO_4$/NaOH, pH 7.5, 30 mM NaCl and exhaustively dialyzed. The dialysate is centrifuged (13,000×g, 15 min, 4° C.) and filtered (0.2 µm).

Biotinylation of Polyclonal Rabbit IgG

Polyclonal rabbit IgG is brought to 10 mg/ml in 10 mM $NaH_2PO_4$/NaOH, pH 7.5, 30 mM NaCl. Per ml IgG solution 50 µl Biotin-N-hydroxysuccinimide (3.6 mg/ml in DMSO) are added. After 30 min at room temperature, the sample is chromatographed on Superdex 200 (10 mM $NaH_2PO_4$/NaOH, pH 7.5, 30 mM NaCl). The fraction containing biotinylated IgG are collected. Monoclonal antibodies are biotinylated according to the same procedure.

Digoxygenylation of Polyclonal Rabbit IgG

Polyclonal rabbit IgG is brought to 10 mg/ml in 10 mM $NaH_2PO_4$/NaOH, 30 mM NaCl, pH 7.5. Per ml IgG solution 50 µl digoxigenin-3-O-methylcarbonyl-ε-aminocaproic acid-N-hydroxysuccinimide ester (Roche Diagnostics, Mannheim, Germany, Cat. No. 1 333 054) (3.8 mg/ml in DMSO) are added. After 30 min at room temperature, the sample is chromatographed on Superdex® 200 (10 mM $NaH_2PO_4$/NaOH, pH 7.5, 30 mM NaCl). The fractions containing digoxigenylated IgG are collected. Monoclonal antibodies are labeled with digoxigenin according to the same procedure.

EXAMPLE 3

Western Blot for the Detection of CRABP-II in Human Serum and Plasma Samples

SDS-PAGE and Western Blotting are carried out using reagents and equipment of Invitrogen, Karlsruhe, Germany. Human plasma samples are diluted 1:20 in reducing NuPAGE® (Invitrogen) LDS sample buffer and heated for 5 min at 95° C. 10 µl aliquots are run on 4-12% NuPAGE® gels (Bis-Tris) in the MES running buffer system. The gel-separated protein mixture is blotted onto nitrocellulose membranes using the Invitrogen XCell II™ Blot Module (Invitrogen) and the NuPAGE® transfer buffer system. The membranes are washed 3 times in PBS/0.05% Tween-20 and blocked with SuperBlock Blocking Buffer (Pierce Biotechnology, Inc., Rockford, Ill., USA). The biotinylated primary antibody is diluted in SuperBlock Blocking Buffer (0.01-0.2 µg/ml) and incubated with the membrane for 1 h. The membranes are washed 3 times in PBS/0.05% Tween-20. The specifically bound biotinylated primary antibody is labeled with a streptavidin-HRP-conjugate (20 m$U_{ABTS}$/ml in SuperBlock Blocking Buffer). After incubation for 1 h, the membranes are washed 3 times in PBS/0.05% Tween-20. The bound streptavidin-HRP-conjugate is detected using a chemiluminescent substrate (SuperSignal West Femto Substrate, Pierce Biotechnology, Inc., Rockford, Ill., USA) and autoradiographic film. Exposure times varies from 10 min to over night.

EXAMPLE 4

ELISA for the Measurement of CRABP-II in Human Serum and Plasma Samples

For detection of CRABP-II in human serum or plasma, a sandwich ELISA was developed using streptavidin-coated 96-well microtiter plates.

For detection of CRABP-II in human serum or plasma, a sandwich ELISA was developed using streptavidin-coated 96-well microtiter plates.

Twenty microliter of a human serum or plasma sample or a serial dilution of the recombinant CRABP-II protein as standard antigen were incubated with 100 µl biotinylated polyclonal anti-CRABP-II (85-96) antibody (0.1 µg/ml) and with digoxygenylated monoclonal anti-CRABP-II (0.1 µg/ml) in 10 mM phosphate, pH 7.4, 1% BSA, 0.9% NaCl and 0.1% Tween-20. After incubation over night at room temperature, the plates were washed three times with 0.9% NaCl, 0.1% Tween-20. For the detection of antigen-antibody complexes, 100 µl of an monoclonal anti-digoxigenin peroxidase conjugate in 10 mM phosphate, pH 7.4, 1% BSA, 0.9% NaCl and 0.1% Tween-20 were added and incubated for 2 h. The excess of conjugate was removed by washing the plates three times with 0.9% NaCl , 0.1% Tween-20. The amount of bound conjugate was detected by incubation with 100 µl ABTS solution (Roche Diagnostics GmbH, Penzberg, Germany, Catalog No. 11685767) for 30-60 min. The color development was quantified at 405 nm using a ELISA reader. The concentration of CRABP-II in a serum or plasma sample was calculated from the standard curve using a serial dilution of recombinant CRABP-II.

EXAMPLE 5

Marker Evaluation, Sensitivity and Specificity; ROC Analysis to Assess Clinical Utility in Terms of Diagnostic Accuracy Accuracy is assessed by analyzing individual liquid samples obtained from well-characterized patient cohorts. The control collective (see Table 1) contains 50 patients having undergone mammography. 40 patients are found mammography negative and no symptoms of other breast diseases are detected. 5 patients are diagnosed with mastitis (3 of 5 are mammography positive) and 5 patients are diagnosed with microcalcification (all 5 are mammography positive). The sample cohort is summarized in Table 1.

TABLE 1

| Healthy patients Σ | | 50 | |
|---|---|---|---|
| | Healthy controls (mammography negative) | 40 | |
| | Mastitis | 5 | Mammography 3 positive |
| | Microcalcification | 5 | Mammography 5 positive |
| Breast cancer Σ | Stage | 50 | |
| | UICC I | 20 | |
| | UICC II | 19 | |
| | UICC III | 10 | |
| | UICC IV | 1 | |

TABLE 1-continued

| Other cancers | | 120 |
|---|---|---|
| | Colon cancer | 40 |
| | Lung cancer | 20 |
| | Stomach cancer | 20 |
| | Ovary cancer | 20 |
| | Prostate cancer | 20 |

The 50 breast cancer patients were put together from patients with invasive ductal and invasive lobular carcinomas of different stages. Due to the aim to diagnose breast cancer at early stages, the proportion of UICC I and UICC II stages was 78%. To analyze the specificity to other solid tumors a collective of 40 colon, 20 lung, 20 stomach, 20 ovary and 20 prostate cancer samples were also measured. CA 15-3 and CEA as measured by commercially available assays (Roche Diagnostics, CA 15-3-assay: Cat. No. 0 304 5838 and CEA-assay: Cat. No. 1731629) for Elecsys® Systems immunoassay analyzer) and CRABP-II measured as described above have been quantified in a serum obtained from each of these individuals.

The cut-off is defined with respect to the 95% percentile of the control group, equalling 95% specificity. Thus, in the present series of experiments the Cut-off value for CRABP-II is set to 0.92 ng/ml.

It is noted that the 3 positive (assumed to be false-positive) control patients of the CRABP-II measurement in the "healthy control" group are no mastitis or microcalcification patients. Such patients usually give rise to a high rate of positive results based on mammography. It is found that there is no positive reaction in the lung, stomach and prostate cancer group. There are only three positive results in colon cancer patients. This observation is comparable to that of the healthy control group. The most positive reactions are observed in the ovarian cancer group, that is to say 6 out of 20.

The data summarizing sensitivity and specificity of CRABP-II in comparison to the markers CEA and CA 15-3 are given in Table 2 and Table 3.

TABLE 2

| | Sensitivity | | |
|---|---|---|---|
| Number of positive results | CRABP-II | CA 15-3 | CEA |
| UICC I | 4/20 | 1/20 | 1/20 |
| UICC II | 5/19 | 4/19 | 4/19 |
| UICC III | 2/10 | 6/10 | 3/10 |
| UICC IV | 1/1 | 1/1 | 1/1 |
| Total | 12/50 | 12/50 | 9/50 |
| Sensitivity | 24% | 24% | 18% |

TABLE 3

| | Specificity | | |
|---|---|---|---|
| Values given in [%] | CRABP-II | CA 15-3 | CEA |
| Controls | 94 | 90 | 90 |
| Other cancers: | 96 | 90 | 61 |
| Colon + lung + stomach | | | |
| Colon + lung + stomach + ovary | 91 | 81 | 64 |
| Colon + lung + stomach + ovary + prostate | 93 | 79 | 68 |
| All controls | 93 | 82 | 75 |

Figure 2:
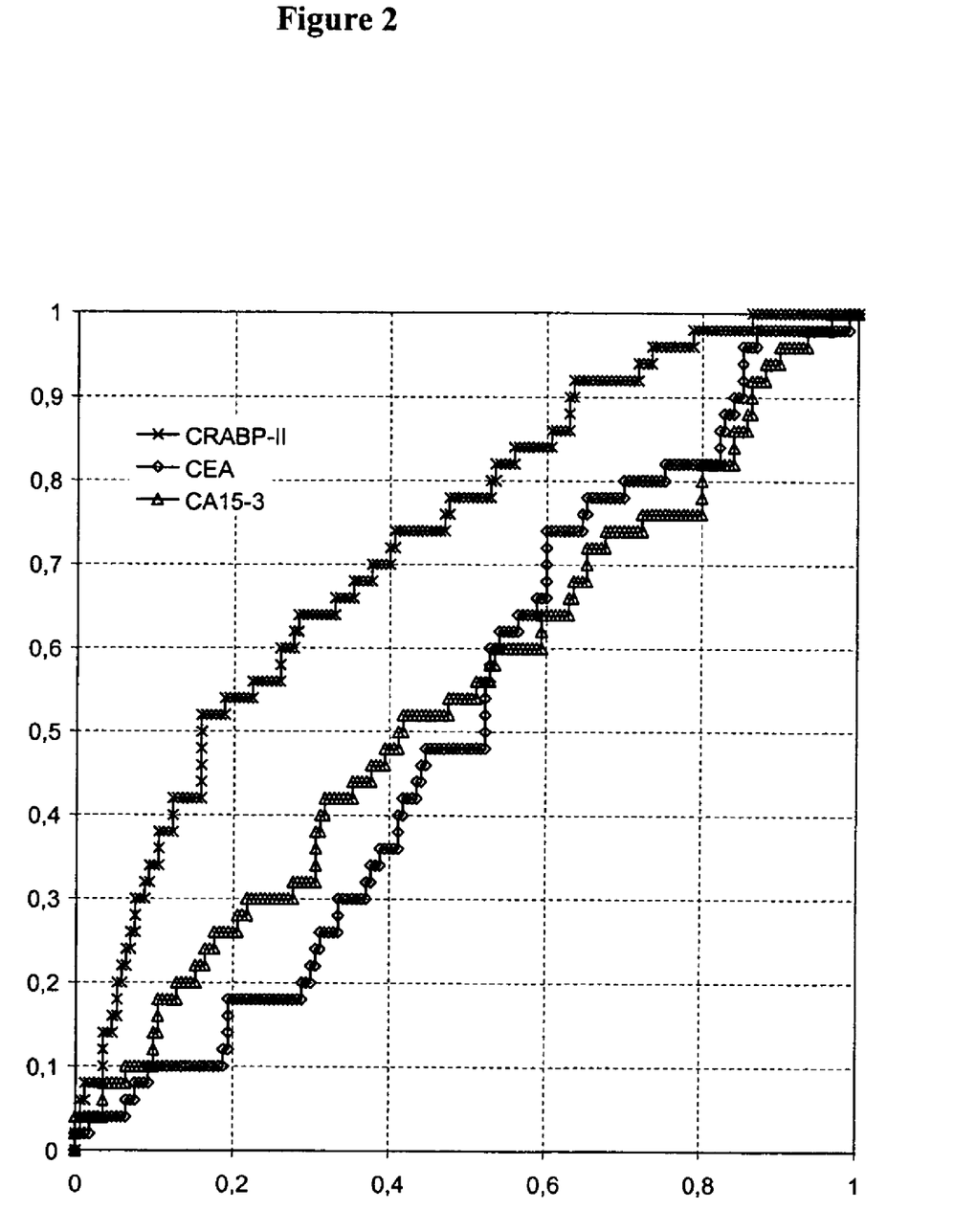
FIG. 2 shows ROC-Curves: Breast Cancer versus Controls/ Others cancers. The x-axis indicates the value computed by subtracting from 1 the specificity value. The y-axis indicates sensitivity. In both the value of 1 corresponds to 100%. The ROC values for CRABP-II, CEA and CA 15-3 have been determined to be 73%, 51%, and 54%, respectively.
Figure 3:
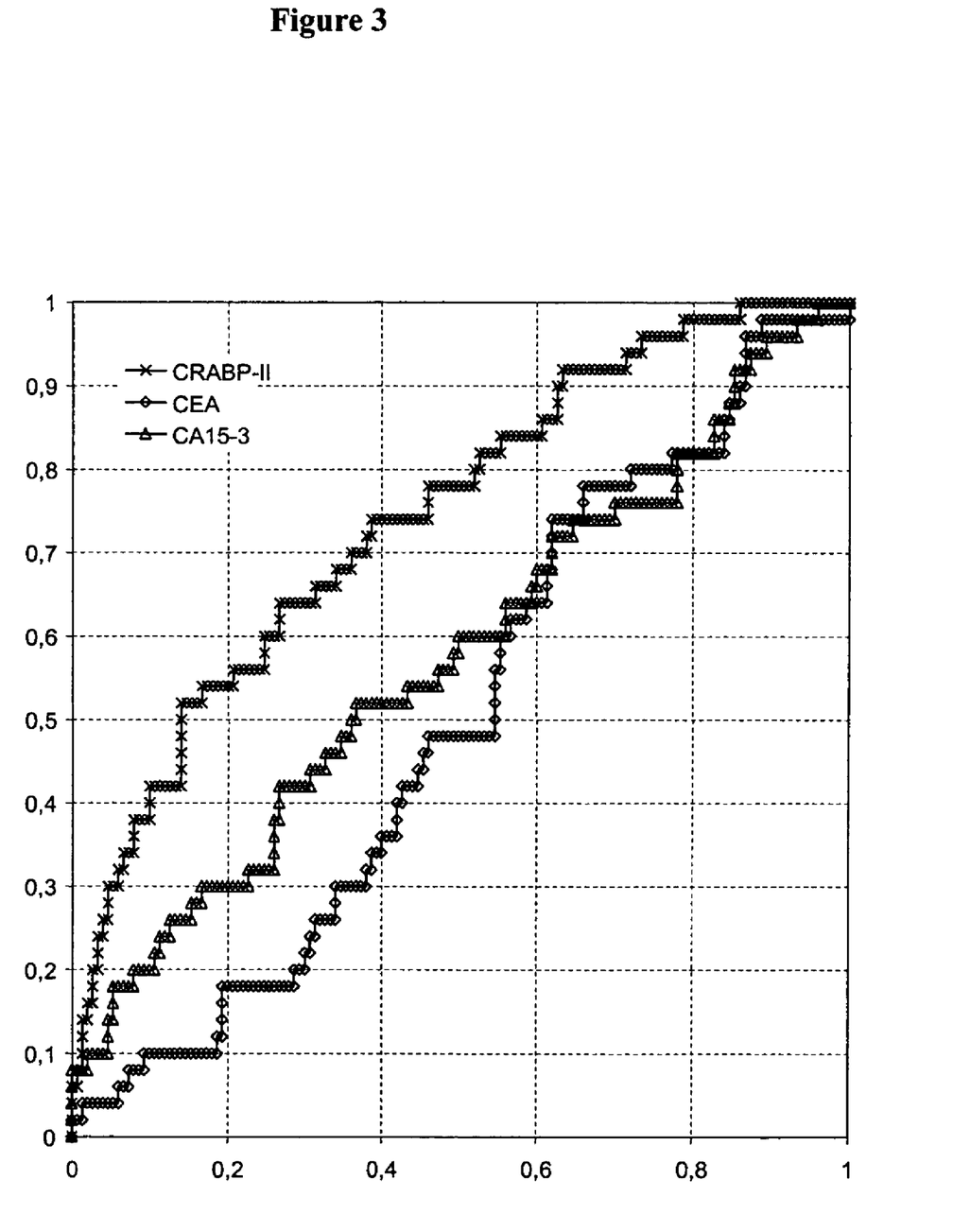
FIG. 3 shows ROC-Curves: Breast Cancer versus Controls/ Other cancers excluding ovary cancer. The x-axis indicates the value computed by subtracting from 1 the specificity value. The y-axis indicates sensitivity. In both the value of 1 corresponds to 100%. The ROC values for CRABP-II, CEA and CA 15-3 have been determined to be 74%, 50%, and 58%, respectively.

ROC-analysis was performed according to Zweig, M. H., and Campbell, supra. Discriminatory power for differentiating patients in the breast cancer group from the "healthy" control group as measured by the area under the curve was found to be at least as good for CRABP-II (64%) as compared to the established markers CA 15-3 (60%) and CEA (65%), respectively. On the other hand CRABP-II showed a high specificity for breast cancer, since there was no positive result in all stomach, lung and prostate cancer samples. In colon cancer only 3 out of 40 samples were positive (comparable to the healthy control group) and in ovary cancer 6 out of 20 were found positive. This leads to an improved discriminating power of CRABP-II (73%) compared to CA 15-3 (54%) and CEA (51%), if the breast cancer collective is compared with all controls including all other solid tumors.

TABLE 4

ROC values

| Values given in [%] | CRABP-II | CA 15-3 | CEA |
|---|---|---|---|
| Breast cancer/controls | 64 | 60 | 65 |
| Breast cancer/controls + other cancers | 73 | 54 | 51 |

In conclusion, CRABP-II is as sensitive as CA 15-3 and at the same time displays a higher specificity in the enlarged control group, i.e. in the control group including other cancers. Furthermore, CRABP-II detects more tumors at early stages. CRABP-II is highly specific for breast tumors. No positive results have been obtained with serum samples obtained from patients with lung, stomach and prostate cancer and only minor positive reactions with samples obtained from patients with colon cancer. In ovary cancer samples the specificity is lower, but still higher than the specificity of the marker CA 15-3. Using all control samples including all other solid tumors the discriminative power of CRABP-II (73%) is higher than for CA 15-3 (54%) and CEA (51%). The data indicate that CRABP-II may also be very helpful in the diagnosis of breast cancer or in the follow-up of patients after surgery.

In some of the samples from BC patients both the levels of CRABP-II as well as the level of CA 15-3 are elevated. In addition, either CRABP-II or CA 15-3 is positive in individual samples obtained from different breast cancer patients. This leads to a higher sensitivity if both markers are measured in a patient sample. If a patient sample is classified as positive in case one of the markers CRABP-II or CA 15-3 is positive, then a sensitivity of 40% is achieved. Due to the high specificity of CRABP-II, the specificity of this combination is comparable to the specificity of CA 15-3 alone. Thus the increased sensitivity of the marker combination CRABP-II and CA 15-3 does not go to the expense of specificity (CA 15-3 alone 75% and the combination 78%).

TABLE 5

Sensitivity

| Number of positive results | CRABP-II and/or CA 15-3 |
|---|---|
| UICC I | 5/20 |
| UICC II | 7/20 |
| UICC III | 7/10 |
| UICC IV | 1/1 |
| Total | 20/50 |
| Sensitivity | 40% |

TABLE 6

Specificity

| Values given in [%] | CRABP-II and/or CA 15-3 |
|---|---|
| Controls | 86 |
| Other cancers: | 86 |
| Colon + lung + stomach | |
| Colon + lung + stomach + ovary | 77 |
| Colon + lung + stomach + ovary + prostate | 76 |
| All controls | 78 |

---

What is claimed is:

1. A method for diagnosing breast cancer comprising the steps of:
   (a) generating a cut-off value of cellular retinoic acid-binding protein II (CRABP-II) diagnostic of breast cancer by (i) quantifying an amount of CRAPB-II in a cohort of breast cancer negative individuals and an amount of CRABP-II in a cohort of breast cancer positive individuals to yield CRABP-II data; (ii) applying receiver-operating characteristic (ROC) analysis to the CRABP-II data; and (iii) determining the cut-off value as an amount of CRABP-II at a percentile greater than or equal to the 95th percentile of the cohort of breast cancer negative individuals;
   (b) providing a serum sample obtained from an individual;
   (c) quantifying an amount of CRABP-II in the serum sample;
   (d) comparing the amount of CRABP-II in the serum sample to the cut-off value; and
   (e) diagnosing breast cancer in the individual when the amount of CRABP-II in the serum sample is greater than the cut-off value.

2. The method of claim 1 wherein quantifying the amount of CRABP-II comprises contacting the sample with a specific binding agent for CRABP-II under conditions appropriate for formation of a complex between the binding agent and CRABP-II.

3. The method of claim 2 wherein the binding agent is an antibody.

4. The method of claim 2 wherein the binding agent comprises a first and second antibody wherein the first antibody is a capture reagent that binds to the cellular retinoic acid-binding protein II and to a solid support, and the second antibody is labeled to be directly or indirectly detectable.

5. The method of claim 2 further comprising the step of contacting said sample with a second specific binding agent that is specific for a second breast cancer marker.

6. The method of claim 5 wherein the second marker is selected from the group consisting of carcinoembryonic antigen (CEA) and CA 15-3.

* * * * *